United States Patent [19]
Sansom

[11] 3,952,869
[45] Apr. 27, 1976

[54] SEALED CONTAINER

[75] Inventor: Michael Sansom, London, England

[73] Assignee: Matburn (Holdings) Limited, London, England

[22] Filed: Oct. 7, 1974

[21] Appl. No.: 512,843

[30] Foreign Application Priority Data
Oct. 11, 1973  United Kingdom............... 47519/73

[52] U.S. Cl................................. 206/363; 206/498; 206/807; 206/813; 220/214; 220/270; 229/51 AS
[51] Int. Cl.².................. B65D 17/20; B65D 77/30
[58] Field of Search ... 206/363–364, 498, 813, 807; 215/250, 273, 305, 7; 220/214, 260, 220/265, 270, 272, 359; 229/48 T, 51 AS

[56] References Cited
UNITED STATES PATENTS

| | | | |
|---|---|---|---|
| 2,747,345 | 5/1956 | Plastino | 220/359 X |
| 2,801,741 | 8/1957 | Harkness et al. | 215/7 X |
| 2,899,347 | 8/1959 | Kindseth | 229/48 T |
| 3,334,776 | 8/1967 | Ellis | 220/260 |
| 3,396,899 | 8/1968 | Strouse et al. | 220/359 X |
| 3,773,205 | 11/1973 | Keeler et al. | 229/48 T X |
| 3,783,996 | 1/1974 | Gerard et al. | 206/364 |

Primary Examiner—Steven E. Lipman
Attorney, Agent, or Firm—William R. Liberman

[57] ABSTRACT

A container for surgical instruments or other articles has a body. One end of the body is closed by a cap. A sealing band seals the cap and the body together in a sterile manner. A welded sealing area is formed by welding together overlying portions of the band whereby a visible blemished area is produced when the seal at the welded area is broken.

1 Claim, 2 Drawing Figures

SEALED CONTAINER

BRIEF SUMMARY OF THE INVENTION

An object of the invention is to provide a container in which articles (e.g. surgical catheters) can be retained in a sterile condition, and which has a seal which if broken or tampered with cannot be restored without leaving a visible indication that someone has tampered with the seal.

Accordingly, the invention provides a container for surgical instruments or other articles comprising a body, a cap fitted to the body and closing one end thereof, a sealing band which seals the cap and the body together in a sterile manner, and a welded sealing area formed by welding together overlying portions of the band whereby a visible blemished area is produced when the seal at the welded area is broken.

According to another aspect of the invention, a container has a body, a cap closing one end of the body and a sealing band wound round the container and overlying a portion of the outer surface of both the cap and the body, the said band having an end portion forming a tab which is welded to the remainder of the band over a localised area smaller than the area of the tab.

DESCRIPTION OF THE ACCOMPANYING DRAWING

FIG. 1 is a sectional view through a sealed container according to the invention, and FIG. 2 is an elevation of part of the same container.

DESCRIPTION OF PREFERRED EMBODIMENTS

Figure 1:
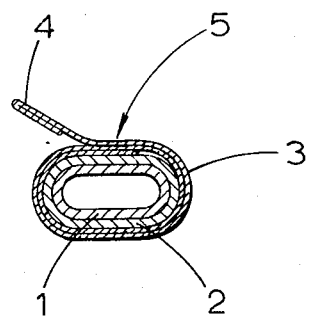
Figure 2:
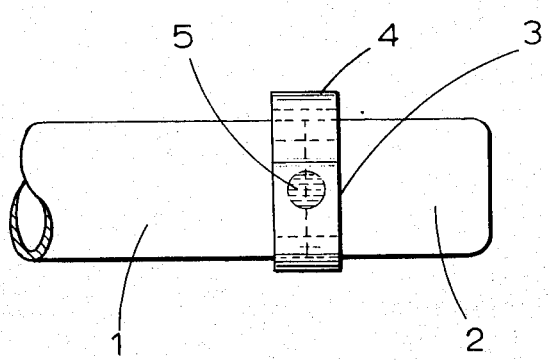

In the illustrated embodiment of the invention, a container for surgical catheters or similar articles comprises a tubular body 1 which is closed at one end and open at the other. A tubular cap 2 fits over the body 1 to close the open end thereof. Both the body 1 and the cap 2 are made of a mouldable plastics material, for example polythene, or polypropylene. A sealing band 3 of self-adhesive tape is wound around the container so as to overlie adjacent portions of both the body 1 and the cap 2 so as to provide a completely occlusive seal. The tape 3 is of weldable thermoplastic material or has a backing of such material. The length of the band 3 is greater than that required to make a single wrap of the container so as to leave a free end portion 4 after the wrap has been complete. This free end portion is folded over on itself to provide a tab. If desired, two or more complete wraps of tape 3 around the container may be made, a free end of the last wrap providing the tab. The tab 4 lies in contact with the remainder of the band 3 and is welded over a localised area 5 smaller than the area of the tab to the remainder of the band, for example by ultra-sonic welding. The unwelded portion of the tab provides an "easy peel" tab portion, but in order to unwind the sealing band 3 it is necessary to tear the tab from the welded area thus creating a blemish in the form of a hole in the tape surface. Thus, it is impossible to disguise the fact that the seal has been broken.

The welded area 5 need not necessarily be in the tab as it may be an area remote from the tab.

What is claimed is:

1. A container for surgical instruments or other articles comprising a body, a cap fitted to the body and closing an end thereof, a sealing band of self-adhesive thermoplastic material spanning the area at which the cap and body abut, the band being wound about the periphery of the body and cap for at least two complete convolutions, which windings seal the cap and the body together in a sterile manner, and a welded sealing area formed by welding together into integral relationship overlying portions of the convolutions of the band whereby a visible blemished area is produced either in the outermost convolution or in the convolution adjacent thereto and underlying same when the seal at the welded area is broken.

* * * * *